US00PP26587P2

(12) United States Plant Patent
Hansen

(10) Patent No.: US PP26,587 P2
(45) Date of Patent: Apr. 5, 2016

(54) ***BAPTISIA* PLANT NAMED 'GRAPE TAFFY'**

(50) Latin Name: ***Baptisia* hybrid**
Varietal Denomination: Grape Taffy

(71) Applicant: Hans Andrew Hansen, Zeeland, MI (US)

(72) Inventor: Hans Andrew Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 165 days.

(21) Appl. No.: 14/120,611

(22) Filed: Jun. 9, 2014

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of interspecific *Baptisia*, 'Grape Taffy', characterized by its deep purple flowers, its compact growth habit, and its hardiness in U.S.D.A. Zones 4 to 8.

2 Drawing Sheets

Botanical classification: *Baptisia* hybrid.
Cultivar designation: 'Grape Taffy'.

BACKGROUND OF THE INVENTION

The present invention relates to a new and distinct cultivar of hybrid *Baptisia* plant, botanically known as *Baptisia* 'Grape Taffy' and will be referred to hereafter by its cultivar name, 'Grape Taffy'. The new cultivar represents a new false indigo, an herbaceous perennial grown for landscape use.

The new invention arose from an ongoing breeding program in Waseca, Minn. The breeding program was established in 1998 with the goal of developing novel interspecific *Baptisia* hybrids with unique and superior garden attributes.

'Grape Taffy' was derived from a cross made in 2004 between an unnamed plant of *Baptisia cinera* as the female parent and an unnamed plant of *Baptisia minor* as the male parent. 'Grape Taffy' was selected in 2008 as a single unique plant amongst the resulting seedlings.

Asexual propagation of the new cultivar was first accomplished by stem cuttings in early June of 2008 in Zeeland, Mich. under the direction of the Inventor. Asexual propagation by stem cuttings and tissue culture has determined that characterisitcs of the new cultivar are stable and are reproduced true to type in successive generations.

SUMMARY OF THE INVENTION

The following traits have been repeatedly observed and represent the characteristics of the new cultivar as observed for five years in Waseca, Minn. These attributes in combination distinguish 'Grape Taffy' from other varieties of *Baptisia* known to the inventor.

1. 'Grape Taffy' exhibits flowers that are deep purple in color.
2. 'Grape Taffy' exhibits blue-green foliage.
3. 'Grape Taffy' has a short, upright to mounded and compact growth habit.
4. 'Grape Taffy' is hardy in U.S.D.A. Zones 4 to 8.

In comparison to the female parent, an unnamed plant of *Baptisia cinera,* 'Grape Taffy' has deep purple flowers with a yellow keel whereas the female parent has creamy white flowers, 'Grape Taffy' also has a more compact growth habit and displays flowers that are more upright compared to the flowers of the female parent that are held at a 45° angle. In addition, the flower spikes of 'Grape Taffy' are longer than those of the female parent. In comparison to the male parent, an unnamed plant of *Baptisia minor,* 'Grape Taffy' has deep purple flowers with a yellow keel, whereas the male parent has blue flowers. The flower spikes of the male parent remain erect throughout the flower sequence whereas the flowers of 'Grape Taffy' arch towards the end of the flower sequence. The closest comparison cultivars are *Baptisia* 'Twilite' (U.S. Plant Pat. No. 19,011) and *Baptisia* 'Purple Smoke' (not patented). 'Twilite' is also an interspecific hybrid, however it has violet-purple colored flowers, and is much taller in height; reaching 5 feet whereas 'Grape Taffy' matures to about 2 feet. 'Purple Smoke', which is also an interspecific hybrid, differs from 'Grape Taffy' in having lighter violet colored flowers, a taller growth habit and dark gray stems.

BRIEF DESCRIPTION OF THE DRAWING

The accompanying colored photographs illustrate the overall appearance and distinct characteristics of the new *Baptisia*. The photographs were taken of plants and plant parts of a plant four years in age as grown outdoors in Waseca, Minn.

The photograph in FIG. 1 provides a view of a plant of 'Grape Taffy' in bloom and illustrates the dense, uniform habit and the abundance of flowers stems.

Figure 1:
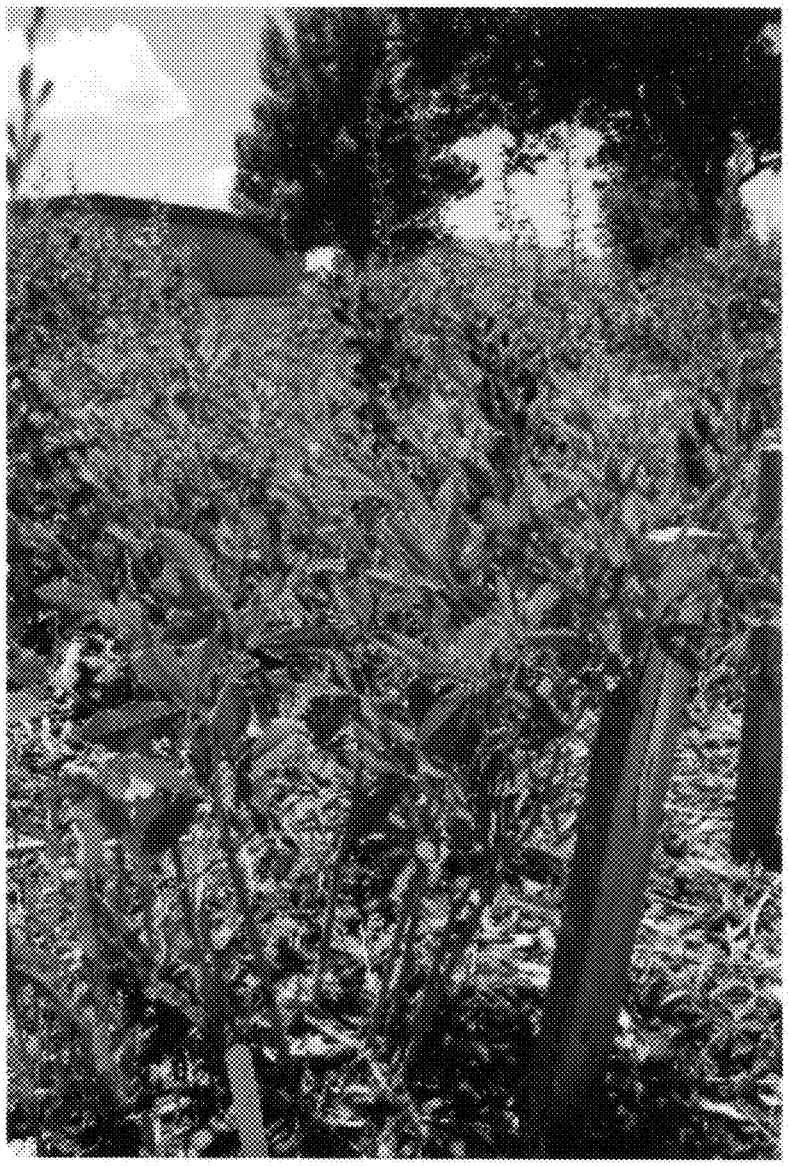
Figure 2:
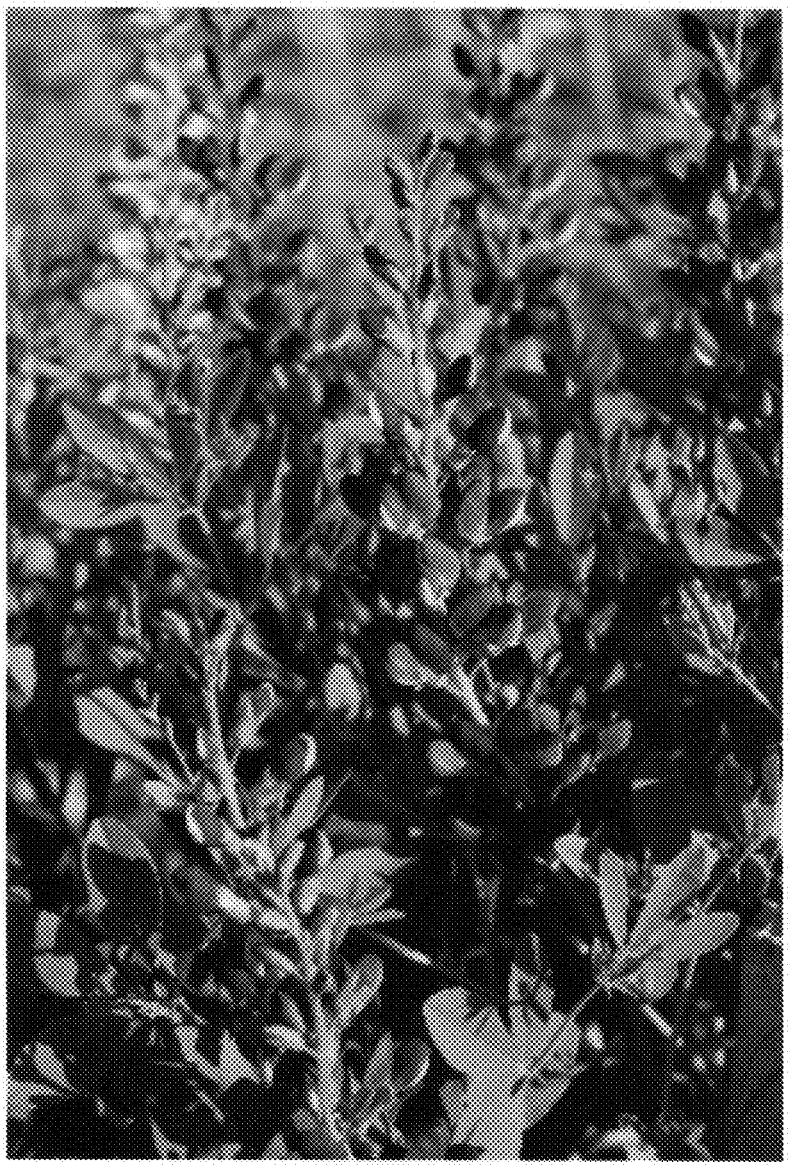

The photograph in FIG. 2 provides a close-up view of the flowers of 'Grape Taffy'.

The colors in the photographs may differ slightly from the color values cited in the detailed botanical description, which accurately describe the colors of the new *Baptisia.*

DETAILED BOTANICAL DESCRIPTION OF THE PLANT

The following is a detailed description of 4 year-old plants of the new cultivar as grown outdoors in a trial plot in Waseca, Minn. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period*.—Typically June 7th through July 12th in Waseca, Minn.

*Plant habit*.—Compact and upright.

*Height and spread*.—Reaches 50 cm width and 58 cm in height.

*Hardiness*.—U.S.D.A. Zones 4 to 8.

*Culture*.—Prefers well-drained to medium moist soils in full sun, tolerant to lean soils and drought.

*Diseases and pests*.—No susceptibility to diseases or pests has been observed.

*Root description*.—Deep rooted, fibrous.

*Propagation*.—Stem cuttings, tissue culture is also possible.

*Growth rate*.—Moderate.

Stem description:

*Branch habit*.—Very densely branched; average of 7 branches with an average of 6 secondary branches, and 3 tertiary branches per secondary branch.

*Stem size*.—Main stem; average of 51 cm (including peduncle) in length and 4 mm in width (8 mm at base), secondary; average of 30 cm in length and 4 mm in width, tertiary; an average of 10 cm in length and 2 mm in width.

*Stem shape*.—Oval.

*Stem color*.—144A to 144B.

*Stem surface*.—Hairless, satiny but slightly glaucous.

Foliage description:

*Leaf shape*.—Fan-shaped in overall outline.

*Leaf division*.—3-palmate.

*Leaf internode*.—Foliage begins 10 cm from base, an average of 4.5 cm on main stem and secondary branches.

*Leaf size*.—About 4.7 cm in length and 8.3 cm in width.

*Leaf quantity*.—About 69 per stem.

*Leaflet shape*.—Oblanceolate.

*Leaflet base*.—Cuneate.

*Leaflet apex*.—Broadly acute.

*Leaflet venation*.—Pinnate pattern, not conspicuous, color matches leaflet color on the upper and lower surface with the mid rib of lower surface 146D.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded upper and lower surface; 146B, mature; upper and lower surface 137A.

*Leaflet size*.—An average of 4.7 cm in length and 1.8 cm in width.

*Petioles*.—Average of 1 cm in length and 1.5 mm in width, clasping to stem at mature nodes, 146C in color, surface is glabrous and satiny.

*Stipules*.—Narrowly lanceolate in shape, reflexed to stem, base is truncate to stem, apex is apiculate, average of 1.7 cm in length and 3 mm in width on mature leaves, 137A in color on upper surface and 137B on lower surface.

Flower description:

*Inflorescence type*.—Terminal racemes of pea-like flowers on main with smaller racemes on secondary branches, blooms from the base to the apex.

*Inflorescence size*.—Average of 19.8 cm in length and 5.5 cm in width in mid section.

*Lastingness of inflorescence*.≥3 to 4 weeks.

*Flower size*.—About 2.5 cm in depth and about 2 cm in diameter.

*Flower fragrance* .—Faint.

*Flower number per inflorescence*.—About 28.

*Peduncle*.—Oval in shape, up to 22 cm in length and an average of 3 mm in width, 144A to 144B in color, surface is glabrous, satiny and slightly glaucous, flower internode length averages about 5 mm.

*Petiole*.—About 9 mm in length, about 1.5 mm in width, oval in shape, color 137B, glabrous and satiny surface.

*Flower buds*.—Kidney-shaped, about 2.2 cm in length and 8 mm in width, color of petal portion is 79A with exposed keel portion 2C, calyx portion same as open flowers.

*Flower type*.—Papilionaceous, held at about a 30° angle to stem (0° vertical).

*Calyx*.—Campanulate, about 1 cm in length and 6 mm in diameter, surface is glabrous and satiny, 144A in color suffused with N186A to 147A, persistent.

*Sepals*.—5, fused with the exception of apex of each, free portion is triangular in shape 3 mm in width and 3 mm in depth with an acute apex, 147B in color suffused with 79A.

*Corolla features*.—Papilionaceous (4 segments) with a keel, a banner and 2 lateral wings, lateral wings; obelliptic in shape, flared to expose keel, about 2.3 cm in length and 7 mm in width, color on outer surface 79A and inner surface 79B with the basal portion 157C, rounded apex, oblique base, keel; only partially visible, comprised of 2 segments surrounding reproductive organs, oblong (slightly oblique) in shape with rounded apex and oblique base, 2.2 cm in length and 1 cm in width, upper surface and lower surface are 160C in color with apex suffused with 73A, banner; orbicular in shape and partially reflexed, about 1.9 cm in length and 1.6 cm in width, upper and lower surface is 79A with the basal portion 145B and 150C, apex is rounded with a single notch, surface is glabrous on all sections.

*Receptacle*.—Disk-shaped, gelatinous, 144A in color, about 3 mm in diameter and 1.2 mm in depth.

Reproductive organs:

*Gynoecium*.—1 Pistil, about 2 cm in length, 1.7 mm in width; style is 144C in color and 8 mm in length; stigma minute, too small to read color, ovary is superior with a stipe, 144A in color, 8.5 mm in length and 1.7 mm in width; stipe is 144C in color, 4 mm in length and 1 mm in width.

*Androecium*.—10 stamens, not united, 2 cm in length and 1 mm in width, filament is 1.9 cm in length, 1 mm in width and 145C in color; anther is dorsifixed, many amorphously shaped, about 1 mm in length and width and 165C in color, pollen is not distinguishable.

*Fruit and seed*.—An inflated pod; 10 produced per inflorescence (open pollinated), oblong in shape, an average of 40 mm in length and 10 mm in width, color of outer surface when mature in early September 165D with spots of 202A, color of inner surface 156 B, dull and rough surface, wall about 1 mm, seed; about 6 per fruit (open-pollinated), color 164D with shades of 164A, oval in shape with the hilum side more or less straight, seed compressed to flattish, 4 mm in length, 3 mm in width and 1.5 mm in thickness.

It is claimed:

1. A new and distinct cultivar of *Baptisia* plant named 'Grape Taffy' as herein illustrated and described.

* * * * *